US00PP26903P3

(12) United States Plant Patent
Bacon

(10) Patent No.: US PP26,903 P3
(45) Date of Patent: Jul. 5, 2016

(54) GRAPEVINE PLANT NAMED 'SUGRAFORTYSIX'

(50) Latin Name: *Vitis vinifera*
Varietal Denomination: Sugrafortysix

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 116 days.

(21) Appl. No.: 14/121,715

(22) Filed: Oct. 10, 2014

(65) Prior Publication Data

US 2016/0106015 P1 Apr. 14, 2016

(51) Int. Cl.
*A01H 5/08* (2006.01)

(52) U.S. Cl.
USPC ..... Plt./205

(58) Field of Classification Search
USPC ..... Plt./205
See application file for complete search history.

*Primary Examiner* — Anne Grunberg

(74) *Attorney, Agent, or Firm* — Knobbe, Martens, Olson & Bear, LLP

(57) ABSTRACT

A new and distinct grapevine variety 'Sugrafortysix' is characterized in that it produces large, red and ovoid berries and has a large bunch size. The berries of 'Sugrafortysix' are firm and very juicy. The new variety 'Sugrafortysix' is characterized by an earlier harvest date compared to 'Scarlet Royal' (U.S. Plant Pat. No. 16,229).

1 Drawing Sheet

Latin name of the genus and species claimed: *Vitis vinifera*. Variety denomination: 'SUGRAFORTYSIX'.

BACKGROUND AND SUMMARY OF THE INVENTION

This invention relates to the discovery and asexual propagation of a new and distinct variety of grapevine, 'Sugrafortysix', as herein described and illustrated. The new variety was first selected as breeder number 'GR402R' by Terry A. Bacon in Wasco, Kern County, Calif. in July 2013. The variety was originated by controlled hybridization.

The new variety 'Sugrafortysix' is characterized by an early harvest date, the production of a large-sized, red, ovoid berry and a large bunch size. The berries of 'Sugrafortysix' are firm and very juicy.

The seed parent is the varietal selection 'Sugrathirtyfive' (U.S. Plant Pat. No. 20,491) and the pollen parent is an unknown breeding variety from bulk pollen. The parent varieties were first crossed in May 2011. The date of first sowing was March 2012, and the date of first flowering was May 2013.

The new variety 'Sugrafortysix' was first asexually propagated in December 2013 in Wasco, Kern County, Calif., by Terry A. Bacon using hardwood cuttings.

The new variety 'Sugrafortysix' differs from its seed parent 'Sugrathirtyfive' (U.S. Plant Pat. No. 20,491) in that the berries of the new variety are red compared to the green berries for 'Sugrathirtyfive' (U.S. Plant Pat. No. 20,491).

The berry color of the new variety 'Sugrafortysix' is similar to 'Scarlet Royal' (U.S. Plant Pat. No. 16,229). However, the harvest start date of the new variety 'Sugrafortysix' is about August 11 compared to August 20 for 'Scarlet Royal' (U.S. Plant Pat. No. 16,229). Additionally, the new variety 'Sugrafortysix' has an ovoid berry shape compared to an elongated berry shape for 'Scarlet Royal' (U.S. Plant Pat. No. 16,229).

The new 'Sugrafortysix' variety has been shown to maintain its distinguishing characteristics through successive asexual propagations by, for example, cuttings.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafortysix'.

The illustration shows the upper and lower surface of the leaves and exterior and sectional view of the fruit.

The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to 'Sugrafortysix' plants grown in the vicinity of Wasco, Kern County, Calif. during 2014, and is believed to apply to plants of the variety grown under similar conditions of soil and climate elsewhere.

VINE

General: (Measurements taken on a mature vine in its 3rd leaf from planting unless otherwise noted. Vines were planted in March 2012).

*Practices*.—Gene-pool-vine: Cane pruned to approximately 6 spurs per vine. Test-vines: Cane pruned to approximately 6 spurs per vine.

*Size*.—Medium. Height: Medium, Approximately 2.0 m. Width: Approximately 2.2 m.

*Vigor*.—Medium.

*Fresh pruning weight*.—Approximately 7.5 kg per vine.

*Density of foliage*.—Medium.

*Productivity*.—Productive — approximately 44 clusters per vine after thinning.

*Yield*.—Approximately 28.6 kg per vine.

*Crop load*.—Approximately 3.8 kg per vine (kg fruit per kg fresh-pruning-weight).

*Own root*.—Yes.

*Resistance*.—Neither resistance nor susceptibility to diseases or pests has been observed in this variety.

Trunk:

*Shape*.—Circular.

*Diameter*.—Approximately 92 mm.

*Straps*.—Short.

*Surface texture*.—Shaggy.

*Inner bark color*.—Near Medium Greyed-Orange 165C.

*Outer bark color*.—Near Dark Greyed-green 197B.

SHOOTS

Young shoot:

*Form of tip*.—Half open.

*Distribution of anthocyanin coloration of tip*.—Striped.

*Intensity of anthocyanin coloration of tip*.—Weak.

*Density of prostrate hairs on tip*.—Medium.

*Density of erect hairs on tip*.—Absent or very sparse.

Woody shoot (mature canes):

*Shape*.—Slender.

*Internode length*.—Approximately 132 mm.

*Width at node*.—Approximately 13 mm.

*Cross section*.—Circular.

*Surface*.—Smooth.

*Main color*.—About Medium Greyed-Orange 165C.

*Lenticels*.—Absent.

*Density of erect hairs on nodes*.—Absent or Very Sparse.

*Density of erect hairs on internodes*.—Absent or Very Sparse.

*Growth of auxiliary shoots*.—Average 19.7 cm/shoot.

Flowering shoot:

*Vigor during flowering*.—Medium.

*Attitude during flowering on shoots which are not tied*.—Semi-erect.

*Color of dorsal side of internodes*.—About Light Green 139D.

*Color of ventral side of internodes*.—About Light Green 139D.

*Color of dorsal side of nodes*.—About Light Green 139D.

*Color of ventral side of nodes*.—About Light Green 139D.

*Density of erect hairs on nodes*.—Absent or very sparse.

*Erect hairs on internode*.—Absent or very sparse.

*Density of prostrate hairs on nodes*.—Absent or very sparse.

*Density of prostrate hairs on internodes*.—Absent or very sparse.

*Anthocyanin coloration of buds*.—Absent or very sparse.

Tendrils:

*Distribution on the shoot at full flowering*.—Discontinuous.

*Thickness*.—Medium.

*Color*.—Near Medium Yellow-Green 144C.

*Form*.—Bifurcated.

*Number of consecutive tendrils*.—Up to 2.

*Length of tendril*.—Medium, approximately 9 cm.

LEAVES

Young leaves:

*Color of upper surface of first 4 distal unfolded leaves*.—About Medium Green 141A.

*Average intensity of anthocyanin coloration of six distal leaves prior to flowering*.—Absent or very sparse.

*Density of prostrate hairs between veins at lower surface of 4th distal unfolded leaf*.—Absent or very sparse.

*Density of erect hairs between veins at lower surface of 4th distal unfolded leaf*.—Absent or very sparse.

*Density of prostrate hairs on veins at lower surface of 4th distal unfolded leaf*.—Absent or very sparse.

*Density of erect hairs on veins at lower surface of 4th distal unfolded leaf*.—Absent or very sparse.

Mature leaves:

*Average length*.—Approximately 93 mm.

*Average width*.—Approximately 125 mm.

*Size of blade*.—Medium.

*Shape of blade*.—Pentagonal.

*Number of lobes*.—Approximately 5.

*Anthocyanin coloration of main veins on the upper side of the blade*.—Absent or very faint.

*Mature leaf profile*.—Flat.

*Blistering surface of blade upper surface*.—Absent.

*Leaf blade tip*.—In the plane of the leaf.

*Undulation of margin*.—Slight.

*Thickness*.—Medium.

*Undulation of blade between main and lateral veins*.—Absent or very slight.

*Shape of teeth*.—Mixture of both sides straight and both sides convex.

*Length of teeth*.—Mostly Medium, irregular, varies from 2 mm to 9 mm.

*Ratio length/width of teeth*.—Small, about 0.7.

*General shape of petiole sinus*.—Wide open.

*Tooth at petiole sinus*.—Absent.

*Petiole sinus limited by veins*.—Absent.

*Shape of upper lateral sinus*.—Open.

*Depth of upper lateral sinus*.—Shallow.

*Density of prostrate hairs between veins on lower surface of blade*.—Absent.

*Density of erect hairs between veins on lower surface of blade*.—Absent.

*Density of prostrate hairs on main veins on lower surface of blade*.—Absent.
*Density of erect hairs on main veins on lower surface of blade*.—Absent.
*Density of prostrate hairs on main veins on upper surface of blade*.—Absent.
*Autumn coloration of leaves*.—Varies by year, about Medium Yellow-green 153D and Medium Greyed-yellow 162A.

Upper surface:
*Color*.—About Dark Green 136A.
*Surface texture*.—Smooth.
*Surface appearance*.—Dull.
*Glossiness*.—Weak.
*Pubescence*.—Absent.

Lower surface:
*Color*.—About Medium Green 139C.
*Anthocyanin coloration of main veins on lower leaf surface*.—Absent.
*Glossiness*.—Weak.
*Pubescence*.—Absent.
*Surface texture*.—Smooth.
*Surface appearance*.—Dull.

Petiole:
*Length of petiole*.—Medium, approximately 7 cm.
*Length of petiole compared to middle vein*.—Slightly shorter.
*Diameter*.—Approximately 2.5 mm.
*Density of prostrate hairs on petiole*.—Absent.
*Density of erect hairs on petiole*.—Absent.
*Color*.—Light Green 138D with Medium Red 42 B in areas where exposed to direct sunlight.

Buds:
*Shape*.—Conical.
*Size*.—Medium, approximately 3 mm×4 mm.
*Position*.—Slightly held out.
*Cane bud fruitfulness*.—Basal most fruitful, $4^{th}$ to $5^{th}$ bud position.
*Time of bud burst*.—Medium.

FLOWERS

General:
*Flower sex*.—Hermaphrodite.
*Length of first inflorescence*.—Medium, about 13 cm.
*Position of first flowering node*.—Fourth node.
*Number of inflorescences per shoot*.—Approximately 1 to 2.
*Date of full bloom*.—Approximately May 10th.
*Size (diameter of fully open flower)*.—Medium, approximately 6 mm.

FRUIT

General:
*Ripening period*.—Medium starting about August 11 with mid-ripe August 16.
*Use*.—Fresh market.
*Keeping quality*.—Good.
*Shipping quality*.—Good.
*Date of first harvest*.—Approximately August $11^{th}$.
*Solids-sugar*.—High, about 19%.
*Refractometer test*.—Approximately 19%.
*Acid*.—Medium, approximately 0.54 gr./L tartaric acid.
*Juice pH*.—Approximately 3.5.
*Tendency to crack*.—Low.
*Sensitivity to sunburn*.—Low.
*Fruit shrivel after ripe*.—Absent.
*Secondary cluster*.—Occasional.

Cluster:
*Bunch size (peduncle excluded)*.—Large, about 650 gm.
*Bunch length (peduncle excluded)*.—Medium, approximately 17 cm.
*Bunch width*.—Approximately 15 cm.
*Bunch weight*.—High, approximately 650 g.
*Bunch density*.—Medium.
*Number of berries*.—Approximately 80-100 berries, usually 85.
*Form*.—Conical shouldered.

Peduncle:
*Length of peduncle*.—Medium, approximately 25 mm.
*Lignification of peduncle*.—Absent or very slight.
*Color*.—About Medium Green 139C.

Berry:
*Size*.—Large.
*Uniformity of size*.—Uniform.
*Berry weight*.—Heavy, approximately 7.8 gr.
*Gibberellic acid treated*.—Low, 0 ppm to 10 ppm.
*Shape*.—Ovoid.
*Presence of seeds*.—Rudimentary.
*Cross section*.—Round.
*Dimensions*.—Longitudinal axis: Approximately 28 mm. Horizontal axis: Approximately 23 mm.
*Skin color (without bloom)*.—About Dark Red 46A.
*Flesh color*.—About Light Red 36A.
*Juiciness of flesh*.—Very juicy.
*Berry firmness*.—Firm.
*Particular flavor*.—Fruity.
*Bloom (cuticular wax)*.—Medium.
*Pedicel length*.—Medium approximately 7.5 mm.
*Berry separation from pedicel*.—Medium.
*Visibility of hilum*.—Slight.

Skin:
*Thickness*.—Medium.
*Texture*.—Smooth.
*Reticulation*.—Absent.
*Roughness*.—Absent.
*Tenacity*.—Tenacious to flesh.

Seed:
*Number of seeds per berry*.—Usually 2.
*Size*.—Small.
*Color*.—About Light Green 145A, with some becoming about Medium Greyed-Orange 165B as fruit ripens.
*Texture*.—Soft.
*Endosperm*.—Slight.
*Fresh weight of seed-traces/berry*.—Approximately 15 mg.
*Room-dry weight of seed-traces/berry*.—Approximately 3.5 mg.

What is claimed is:

1. A new and distinct variety of grapevine as herein illustrated and described.

* * * * *

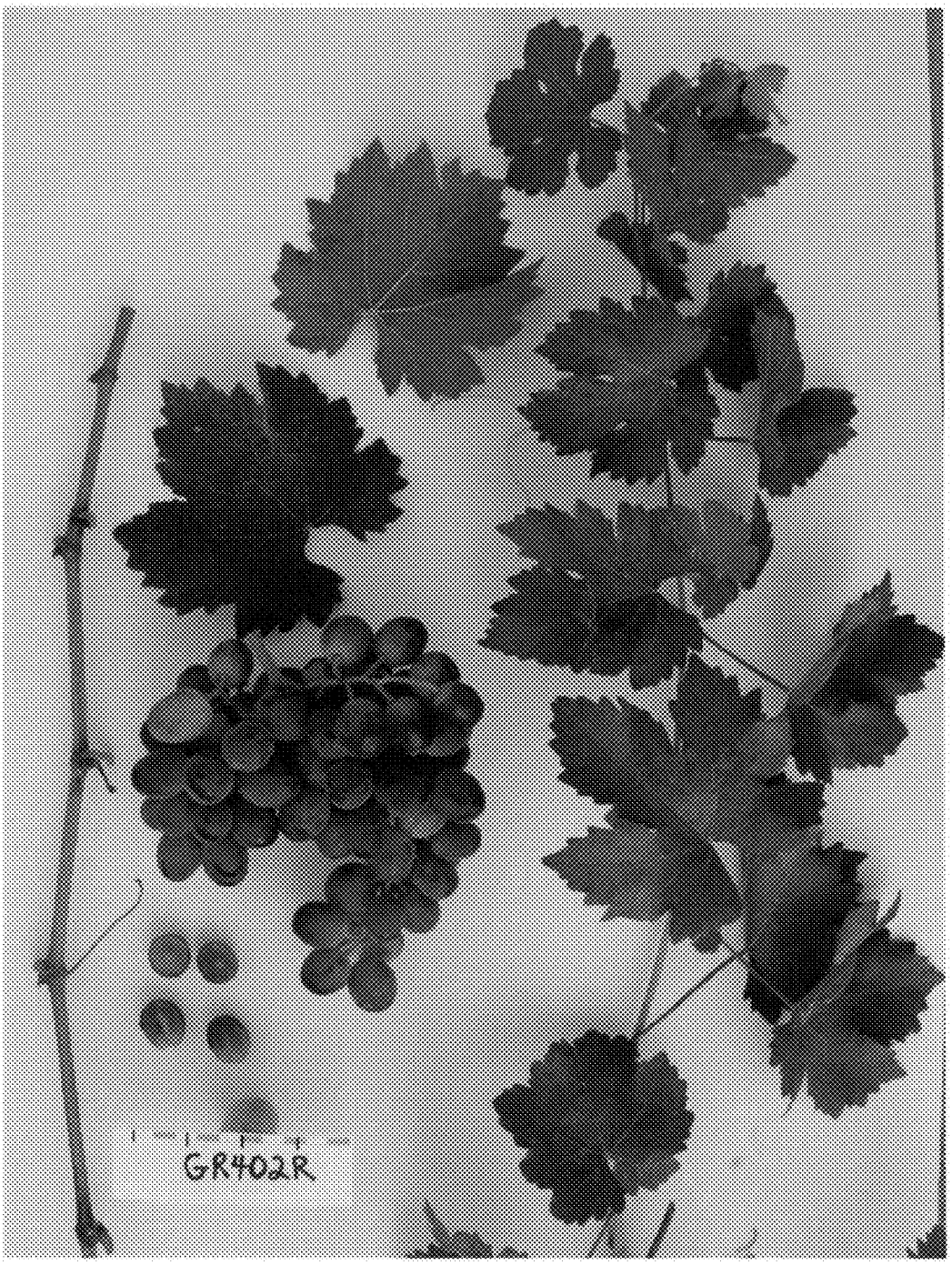
GR402R